(12) United States Patent
Linares (10) Patent No.: US 8,562,550 B2
(45) Date of Patent: Oct. 22, 2013

(54) INTERIOR AND EXTERIOR CAST ASSEMBLIES FOR REPAIRING A BONE FRACTURE AND INCLUDING INTERIOR INFLATABLE OR MECHANICALLY EXPANDABLE INSERTS AS WELL AS EXTERIOR WRAP AROUND AND ADHESIVELY SECURED BRACES

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 449 days.

(21) Appl. No.: 12/785,955

(22) Filed: May 24, 2010

(65) Prior Publication Data

US 2010/0305486 A1  Dec. 2, 2010

Related U.S. Application Data

(63) Continuation of application No. PCT/US2010/036109, filed on May 24, 2010, now abandoned.

(60) Provisional application No. 61/181,510, filed on May 27, 2009.

(51) Int. Cl.
*A61F 5/00* (2006.01)
*A61F 13/00* (2006.01)

(52) U.S. Cl.
USPC ........... 602/5; 602/6; 602/18; 602/13; 602/62

(58) Field of Classification Search
USPC .............. 602/5–8, 60–63, 13; 606/62–63, 60, 606/86–89, 86 R, 297, 68
See application file for complete search history.

(56) References Cited

U.S. PATENT DOCUMENTS

| 4,313,434 | A | 2/1982 | Segal |
| 5,102,413 | A | 4/1992 | Poddar |
| 5,827,289 | A | 10/1998 | Reiley et al. |
| 6,981,981 | B2 | 1/2006 | Reiley et al. |
| 7,052,498 | B2 | 5/2006 | Levy et al. |
| 7,226,481 | B2 | 6/2007 | Kuslich |
| 7,442,195 | B1 | 10/2008 | Behrens |
| 7,601,152 | B2 | 10/2009 | Levy et al. |
| 7,666,205 | B2 | 2/2010 | Weikel et al. |
| 7,670,339 | B2 | 3/2010 | Levy et al. |
| 2003/0176825 | A1* | 9/2003 | Yavnai ............................ 602/13 |
| 2007/0100266 | A1 | 5/2007 | Hargrave et al. |
| 2008/0200855 | A1 | 8/2008 | Pomeroy et al. |
| 2008/0255560 | A1* | 10/2008 | Myers et al. .................... 606/63 |

FOREIGN PATENT DOCUMENTS

| EP | 1820463 A2 | 8/2007 |
| EP | 1913903 A2 | 4/2008 |
| WO | 9856301 A1 | 12/1998 |

* cited by examiner

*Primary Examiner* — Kim M Lewis
(74) *Attorney, Agent, or Firm* — Gifford, Krass, Sprinkle, Anderson & Citkowski, P.C.; Douglas J. McEvoy (57) ABSTRACT

A cast for aligning and supporting first and second bone locations adjoining a bone fracture zone including a body employed in at least one of interior and exterior locations of the bone surrounding the fracture zone. The body provides for at least one of aligning the bone locations on either side of the fracture zone and influencing the bone locations in a compressive fashion against the fracture zone during healing of the bone. The body may further include an internally inserted membrane, such as further exhibiting inflatable bladder incorporating a plurality of elongate stiffening members.

10 Claims, 6 Drawing Sheets

INTERIOR AND EXTERIOR CAST ASSEMBLIES FOR REPAIRING A BONE FRACTURE AND INCLUDING INTERIOR INFLATABLE OR MECHANICALLY EXPANDABLE INSERTS AS WELL AS EXTERIOR WRAP AROUND AND ADHESIVELY SECURED BRACES

CROSS-REFERENCE TO RELATED APPLICATIONS

This application is a continuation of PCT/US10/136,109 filed May 24, 2010, now abandoned and claims the benefit of U.S. Provisional Application 61/181,510 filed on May 27, 2009.

FIELD OF THE INVENTION

The present invention discloses a series of ballasting membranes, braces and exteriorly applied patches, such as which are used with a bone sprain or fracture, and which promote both even alignment and effective healing of the fracture location.

BACKGROUND OF THE INVENTION

The prior art is well documented with cast alignment and positioning devices, the objective of which being to correctly position a broken bone (such as an arm or leg) for correct healing over time. As is well known, incorrect positioning of the broken limbs during the initial healing process can result in the necessity of having to re-break the previously broken limb in order to correctly reposition for subsequent re-healing.

SUMMARY OF THE INVENTION

The present invention discloses a cast for aligning and supporting first and second bone locations adjoining a bone fracture zone and including a body employed in at least one of interior and exterior locations of the bone surrounding the fracture zone. The body provides for at least one of aligning the bone locations on either side of the fracture zone and influencing the bone locations in a compressive fashion against the fracture zone during healing of the bone. The body may further include an internally inserted membrane, such as further exhibiting inflatable bladder incorporating a plurality of elongate stiffening members.

Additional features of the cast membrane further include an interiorly supported and outwardly expandable scissor mechanism. A plurality of clips can also be secured to exterior bone locations adjoining the fracture zone and are actuated to influence the bone locations against the fracture zone.

A patch can also be provided which is constructed of a sufficiently flexible and semi-rigid material for applying over an exterior of the bone. The patch may further include linear end-projecting and serrated engaging straps extending from a first exposed edge and engaging through opposing end situated receiving hooks.

Interior positioned, spaced apart and circumferentially surface extending boundary portions can further be applied along an inner and bone contacting surface of said patch. A settable viscous composition can be administered through a syringe/needle piercing through the patch and into a coaxial and sleeve-shaped interior volume defined between the patch and exposed bone surface, such as between internally projecting boundary portions.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1A:
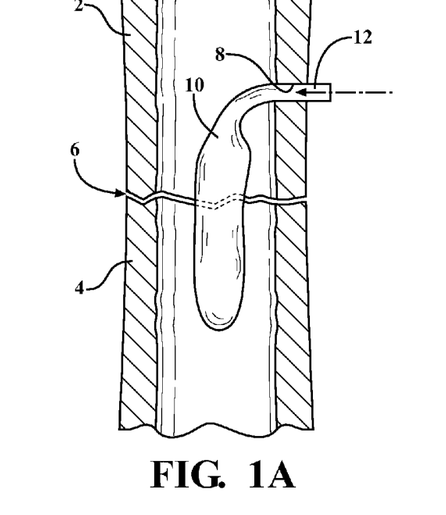
FIG. 1A is a cutaway view of a bone fracture and illustrating a bag-shaped and fillable membrane in a first deflated and pre-inserted position through a side notch aperture formed in the bone proximate the fracture location.

Referring now to FIG. 1A, a cutaway view is shown of first 2 and second 4 bone sections (such as associated with a limb including without limitation an arm or leg), and between which is located a bone fracture zone 6. The break or fracture is further understood to include any of a bone break, partial fracture, sprain, crack or other injury for which alignment of the bone sections is desired during the healing process.

A bag-shaped and fillable/pressurized membrane according to one non-limiting variant of the invention is illustrated at 10 in a first deflated and pre-inserted position through a side notch 8 aperture formed in selected bone section 2 proximate the fracture location. The membrane 10 further exhibits a flexible and expandable bladder (such as constructed from a fluid proof and expandable polymer or like material) and which, following pre-insertion within the bone interior, includes a communicating inlet 12 configured to project through the notch 8 so as to be accessible from an exterior surface of the bone.

Figure 1B:
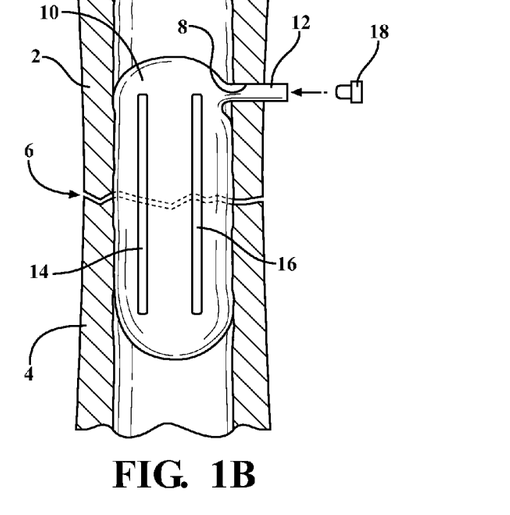
FIG. 1B is a succeeding illustration in which the pre-positioned membrane is aligned so as to extend within the hollow bone interior and inflated such that integrally formed stiffeners contact in adhering fashion along both interior sides of the fracture zone to internally bias, locate and align the bone sections on either side of the fracture zone.

FIG. 1B is a succeeding illustration in which the pre-positioned membrane 10 is aligned so as to extend within the hollow bone interior and along both bone sections 2 and 4 proximate the fracture zone 6. At this point, a nipple (not shown) associated with an external and pressurized fluid supply (such as including air as well as a liquid and/or settable/curable material) is attached to the inlet 12 and inflates the membrane 10 to a substantially expanded position.

Also shown at 14 and 16 are elongated stiffeners which are integrally formed with the membrane 10 (and which can exhibit a sufficient degree of flexibility to permit the initially flaccid membrane to be fitted through the notch 8 and into the bone interior). It is further envisioned and understood that the stiffeners 14 and 16 include being configured upon the exterior surface of the membrane 10, as well as incorporated into its material body between inner and outer surfaces, or supported upon the inside surfaces of the membrane walls.

Upon correct positioning of the initially deflated membrane 10 within the bone break in the manner described, the desired fluid (typically a gas but also contemplated to include a hydraulically charged fluid) is supplied under pressure into the membrane interior and in order to inflate the same. At this point, the membrane inlet 12 is sealed or otherwise capped or closed, and the exterior surfaces of the membrane along with their integrally formed stiffeners 14 and 16 are caused to contact in adhering fashion along both interior sides of the bone fracture zone to internally bias, locate and align the bone sections 2 and 4 on either side of the fracture zone 6.

At this point, the stiffeners 14, 16 prevent the membrane 10 from projecting through the fracture zone 6 during installation and subsequent retention during the bone sealing process. Upon completed healing of the bone sections 2 and 4 at the fracture zone 6, the non-settable fluid composition (or a pneumatic volume such as air) can be withdrawn through the inlet 12 (such as by reattaching an associated hose in a further vacuum inducing condition) following which the membrane 10 is removed through the notch 8 and a permanent cap 18 (see again FIG. 1B) is installed over the notch 8. It is also envisioned that the previously filled/pressurized membrane can be permanently left in place following healing of the bone fracture.

Figure 2A:
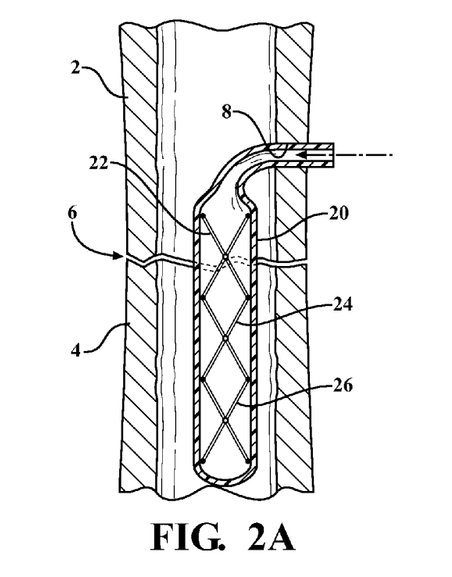
FIG. 2A is a cutaway view of a bone fracture and illustrating an alternately configured membrane similar to that shown in FIG. 1 and illustrated in a pre-inserted position in the bone proximate the fracture location.

Referring now to FIG. 2A, a cutaway view is shown of a similar bone fracture and alternately illustrated membrane 20, this membrane being similar to that shown in FIG. 1 and further being illustrated in a pre-inserted position in the bone proximate the fracture location 6. As also shown in FIG. 2B, which is a succeeding illustration in which the pre-positioned membrane 20 is aligned to extend within the bone across the fracture zone 6, the membrane further incorporates an internally supported and outwardly expandable scissor mechanism, this including individual and interconnected sub-mechanisms 22, 24 and 26, which can be constructed of a rigid plastic or like material.

Similar to the membrane 10 in FIG. 1, the membrane 20 again exhibits a flexible and expandable material. A tool extends through the strategically positioned notch 8 and engages a rotatable input 28 (such as a hex head contact) associated with a first 22 of the interconnected sub-mechanisms, and which are further configured in a mechanically inter-linked fashion such that, upon rotating the input 28, the scissor sub-mechanisms 22, 24 and 26 are caused to outwardly expand in gripping fashion along inside surface locations of the membrane 20 for biasing the membrane 20 in contacting fashion against the inside of the bone on both sides of the fracture zone 6, this occurring concurrent with the mechanism aligning and drawing the bone sections 2 and 4 together against the fracture (see further directional arrows associated with each interconnected scissor sub-section).

Figure 2B:
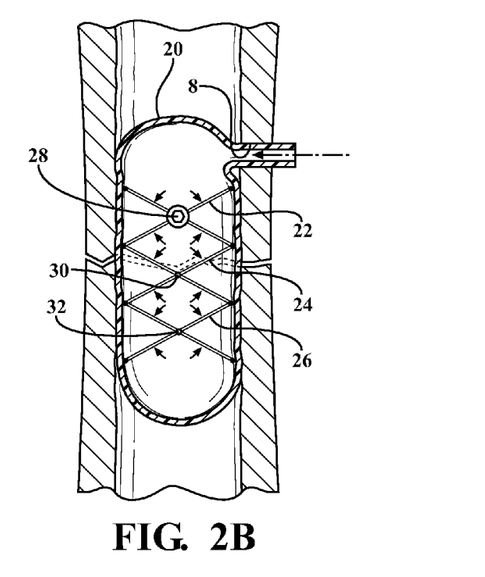
FIG. 2B is a succeeding illustration in which the pre-positioned membrane is aligned to extend within the bone across the fracture zone and incorporates an internally supported and outwardly expandable scissor mechanism for simultaneously gripping inside surface locations of the bone along both sides of the fracture zone, concurrent with aligning and drawing the bone sections together against the fracture.
Figure 3:
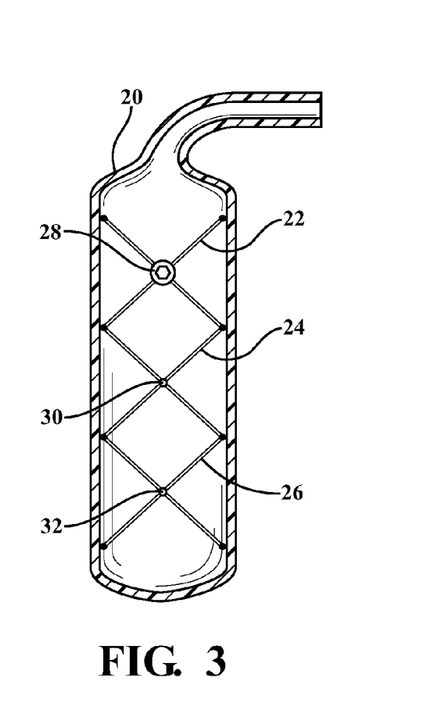
FIG. 3 is an enlarged sectional view of the scissor mechanism supported within the elastic and expandable bladder in an intermediately inflated position between that shown in FIGS. 2A and 2B.

FIG. 3 is an enlarged sectional view of the scissor sub-mechanisms 22, 24 and 26 supported within the membrane 10 in an intermediately inflated position between that shown in FIGS. 2A and 2B. As shown, each interconnected scissor sub-section 22, 24 and 26 exhibits a substantially "X" shape with a pair of stems pivotally interconnected at a central location (see at 28, 30 and 32, respectively) such that the stems are caused to simultaneously draw outwardly against the inner bone surfaces as well as biasing inwardly in opposing fashion toward the fracture zone, such as further illustrated by the directional arrows, and such that the concurrent inner surface contacting and draw together forces are exerted on the bone sections to properly align and bias the bone sections together during natural healing of the fracture. As with the inflatable membrane of FIG. 1, the membrane 20 with scissor mechanism can be either left in place or removed once the bone has healed.

Figure 4A:
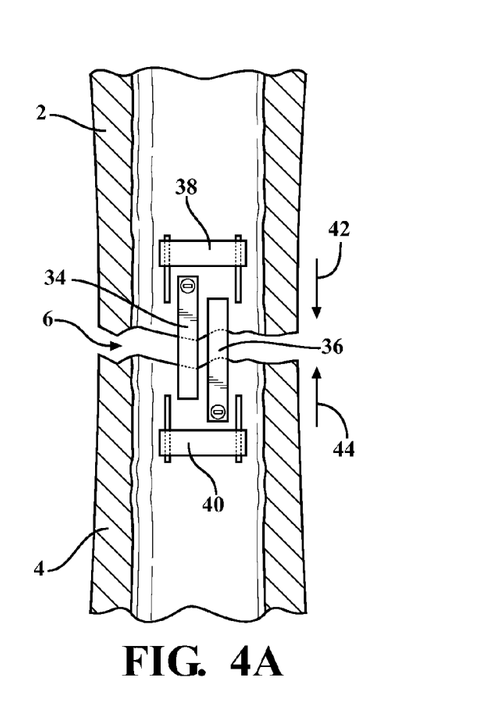
FIG. 4A is a plan illustration of a plurality of exterior mounted clips incorporated into a bone fracture alignment scheme according to a further preferred embodiment and showing first and second bone halves in a first separated position relative an intermediate fracture zone.

Referring now to FIG. 4A, a plan illustration is shown of a plurality of exterior mounted clips 34, 36, 38 and 40 incorporated into a bone fracture alignment scheme according to a further preferred embodiment and again showing first 2 and second 4 bone halves in a first separated position relative an intermediate fracture zone 6. The arrangement of the clips is such that the clips 34 and 36 define a first pair which are mounted, such as by screws or the like, in alternating edge positions relative the bone sections 2 and 4 and such that extending sections of each clip 34 and 36 overlap an edge of the other bone section.

Figure 4B:
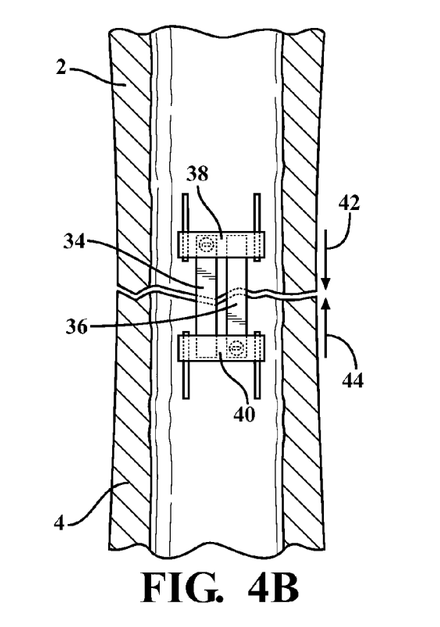
FIG. 4B is a succeeding illustration in which the clips are engaged to draw the bone halves together against the fracture zone.

Additional clips 38 and 40 define a second pair of exterior mounted clips positioned in crosswise extending fashion along each of the bone sections 2 and 4. The second pair of clips 38 and 40 and are capable of being concurrently displaced inwardly (see arrow 42 and 44), such as by an associated sliding or track mechanism (not shown), and in order to abut and contact the offset and overlapping clips 34 and 36, thereby forcing them into the aligned position of FIG. 4B in which the clips are engaged to draw the bone halves 2 and 4 together to align and close the fracture zone 6. At this point, additional screw fasteners (not shown) can be employed in the previously extending/overlapping portions of the clips 34 and 36 and in order to anchor the bone sections 2 and 4 in the aligned/closed position.

Figure 4C:
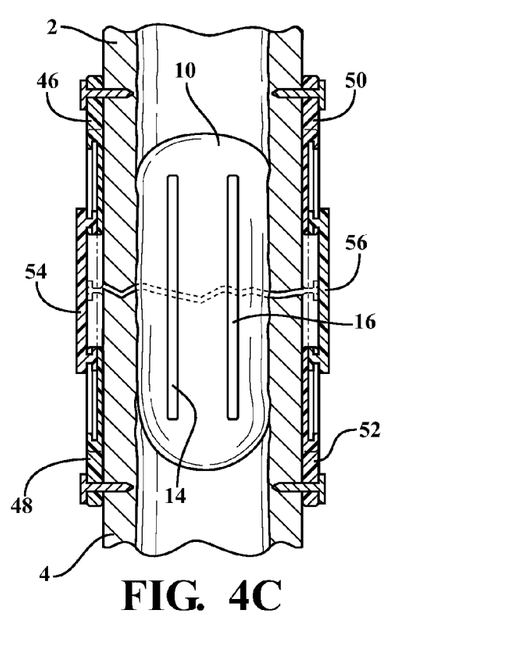
FIG. 4C is an expanded plan view illustrating the clips in use in combination with the internal stiffening and alignment membrane.

FIG. 4C is an expanded plan view illustrating a related variation of spaced apart clips 46 & 48 and 50 & 52 and which are secured by pins to exterior surfaces of the bone sections 2 and 4 at first and second locations. A further pair of overlapping and draw-down portions are provided, see as shown at 54 and 56, which extend across gaps defined between the spaced apart pairs of clips 46-48 and 50-42, respectively in alignment with the fracture zone 6. The overlapping portions 54 and 56 are displaceably engaged with each of the bone surface mounted clips 46 & 48 and 50 & 52 and are further constructed such that relative compressing movement of the bone (consistent with both bone alignment and elimination of the fracture gap 6) results in movement of the anchored clips 46-52 being fixed and uni-directional (i.e. compressive motion results in the surface mounted clips being forced together and not capable of being separated thereafter).

Figure 4D:
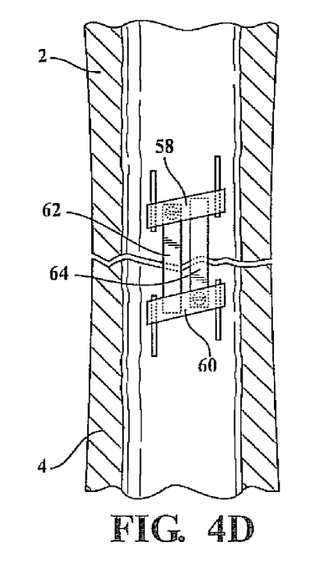
FIG. 4D is an illustration similar to that shown in FIG. 4A of a related clip arrangement employing an angular offset for drawing together the bone halves proximate the fracture zone.

In combination, the internal stiffening and alignment membrane 10 illustrated in FIG. 1 and clip arrangement is employed in the variant of FIG. 4C to align and draw together the bone sections 2 and 4 (this contemplating the overlapping portions 54 and 56 further including a linkage mechanism connecting them to the underlying/fixed clips 45-52, and further such that, upon rotating the overlapping clips 54 and 56 with a suitable tool, a draw-together force is exerted to draw the pairs of clips 46 & 48 and 50 & 52 together), thereby sealing the fracture zone 6 and retaining the bone under a specified degree of compression over an extended period of time corresponding to the healing process. FIG. 4D is an illustration similar to that shown in FIG. 4A of a related clip arrangement as generally shown and in which a pair of end mounted clips 58 and 60 employ an angular offset for drawing together a further pair of linear extending and overlapping clips 62 and 64 secured to respective bone halves proximate the fracture zone.

Figure 5:
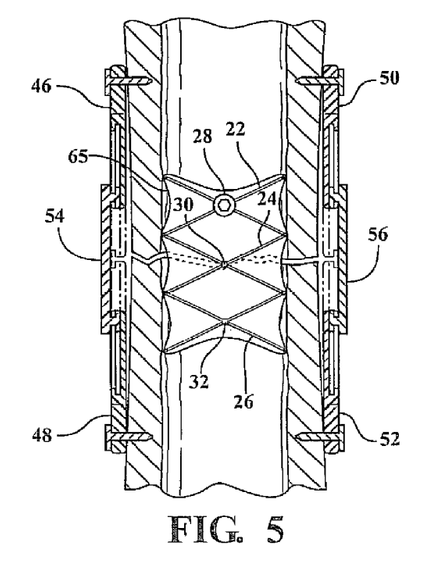
FIG. 5 is an enlarged cutaway plan illustration of an interiorly positioned scissor mechanism incorporated in use with exteriorly supported and draw-together clips for aligning, sealing and supporting a bone fracture according to a still further related variant.

Referring to FIG. 5, an enlarged cutaway plan illustration is shown of a further version of interiorly positioned scissor mechanism (see as previously described in FIG. 2B) and which is incorporated in use with exteriorly supported and draw-together clips (see as previously shown in FIG. 4C) according to another combination of alignment and draw down (fracture gap elimination) support. The arrangement of FIG. 5, in combination, again provides for aligning, sealing and supporting a bone fracture according to a still further related variant.

A flexible support web 65 is illustrated and, similar to the flexible membranes depicted in the earlier variants, contains the individual and interconnected scissor subassemblies 22, 24 and 26. Upon fully expanding the scissor mechanism, and flexing the flexible membrane web 65, it is further envisioned that bone marrow existing inside the bone can agglomerate (or grow) onto the web exterior and which, over time, further strengthens and reinforces the aligned and drawn-down engagement of the fractured bone sections so as to provide additional and long term permanent support to prevent reoccurrence of future damage along the healed fracture zone.

Figure 6A:
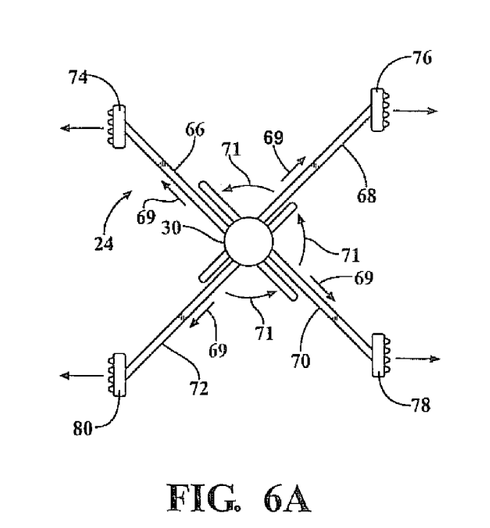
FIG. 6A is an enlarged sectional view of a subset portion of the scissor mechanism shown in FIG. 5 and better illustrating the features of the combined serrated expanding/rotating stems which support end positioned feet for successively contacting and drawing together the inner bone surfaces adjoining the fracture zone.

Referring now to FIG. 6A, an enlarged sectional view is shown of a representative subset scissor mechanism, such as previously generally identified at 24, and which further illustrates one potential and non-limiting arrangement for displacing to an inner bone anchoring condition. The subset mechanism 24 depicts a plurality of combined serrated and expanding/rotating stems, see as shown at 66, 68, 70 and 72 which are outwardly radially displaceable as depicted by arrows 69 in combination with being rotatable a limited range along further arrows 71 relative to central mounting location, again shown at 30.

Although not clearly depicted, the inner engaging ends of the stems 66, 68, 70 and 72 are displaceably seated within the central location 30 in a combined (height) offset and partially overlapping fashion so that the stems do not interfere with one another during their concurrent extension/rotation to an outwardly engaged position. As further shown in FIG. 6B, an enlarged and cutaway view of the central support portion in FIG. 6A further depict the inter engaging serrated configuration established between the location 30 and proximal engaging portions of selected outwardly displaceable and parallel spaced stems 68 and 72.

The engagement structure can further include a one-way ratchet-type arrangement established between inter-engaging locations of the stem and inner extending passageway of the location 30, see as depicted by opposing and engaging serrated edges 73 and 75 illustrated in relation to selected stem 68. A similar serrated engagement is established between each of the stems 68 and 72 (as well as the further pair of stems 66 and 70 which are offset a non-overlapping height and therefore not visible in the particular cutaway of FIG. 6B) and the central location 30.

Figure 6B:
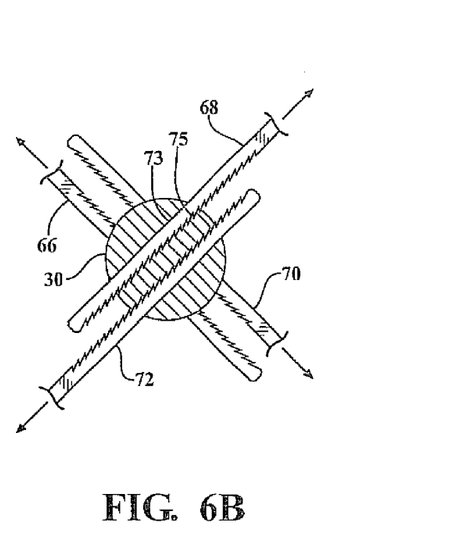
FIG. 6B is an enlarged and cutaway view of the central support portion shown in FIG. 6A and further depicting the inter engaging serrated configuration established between the support and the proximal engaging portions of the outwardly displaceable stems.

The location 30 is further constructed such that it provides a limited degree of swivel/rotatable movement. Also depicted are end positioned feet 74, 76, 78 and 80 (each of which further exhibit gripping surfaces of a frictional retaining nature including such as a rubberized or other suitable composition) which are engaged to extending distal ends of the stems 66, 68, 70 and 72 such that, upon outward displacement of the stems, successively contact and draw together against the inner bone surfaces adjoining the fracture zone.

The central location 30 again illustrates the overlapping serrated nature of the stems 66-72 such that upon application of an appropriate tool or the like, it employs a two-step process to the individual stems which are caused to outwardly and fixedly displace (again in a ratchet-like fashion) to both contact the inner surfaces of the bone sections 2 and 4 and to concurrently influence them into a combined aligning and compressing/sealing fashion, such as either alternatively or in concert with the exterior provided clip engaging mechanism. Following this, the normal healing process again contemplates bone marrow (not shown) growing onto the interior support webs associated with the scissor sub-mechanisms and in order to fixedly anchor the same in place, this also providing the added benefit of increasing the long-term reinforcing support of the bone.

Figure 7A:
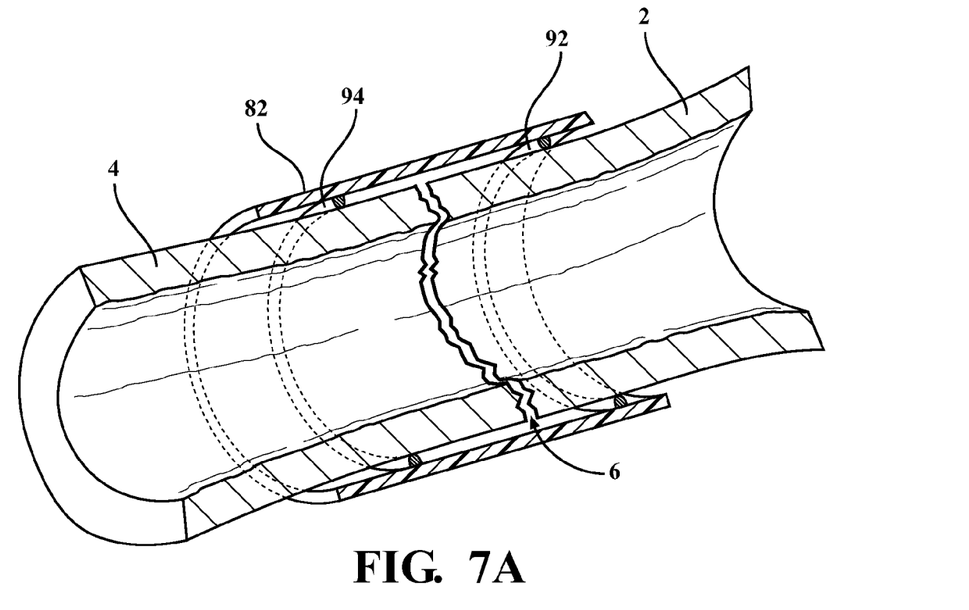
FIG. 7A is a perspective view in partially transparent fashion and illustrating a fracture patch applied to an exterior location of a bone surrounding a fracture zone according to a yet further preferred embodiment.

FIG. 7A is a perspective view in partially transparent fashion and illustrating a fracture patch 82 applied to an exterior location of a bone (e.g. again shown as separated sections 2 and 4 surrounding and separated by a fracture zone 6 according to a yet further preferred embodiment). The patch exhibits a flexible plasticized (including again any type of composite)

material having a generally planar (and as illustrated rectangular mat) shape when unfolded.

Figure 7B:
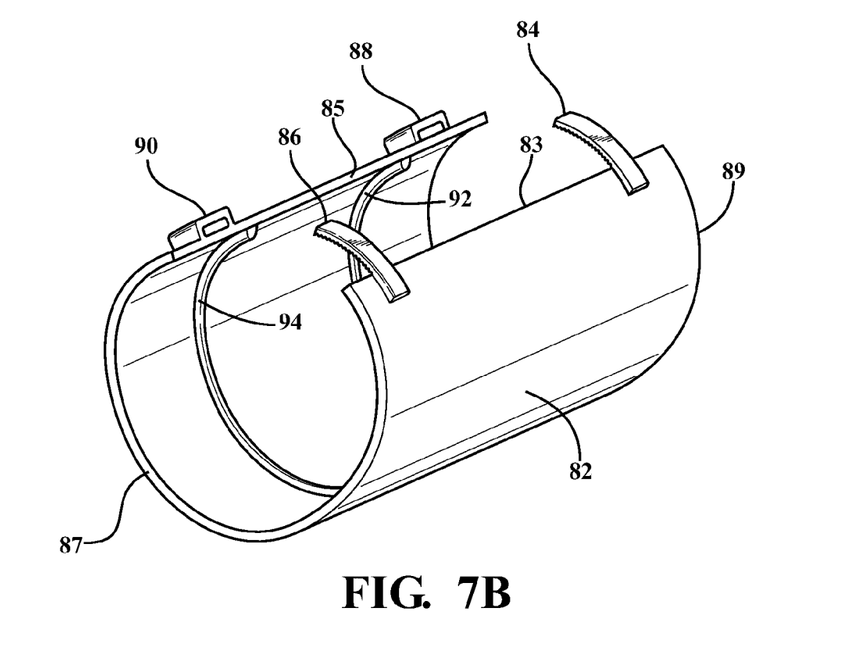
FIG. 7B is a pre-attached position in perspective of the fracture patch and better illustrating the features of the linear end-projecting and serrated engaging straps, combined with interior positioned, spaced apart and circumferentially surface extending boundary portions.

As further shown in FIG. 7B, which is a pre-attached position in perspective of the fracture patch 82, better illustrated are the features of linear end-projecting and serrated engaging straps 84 and 86, these extending from one split edge 83 of the patch 82 and engaging through opposing end situated receiving hooks 88 and 90 disposed in proximity to an opposing split edge 85. Additional features include interior positioned, spaced apart and circumferentially surface extending boundary portions 92 and 94, these including such as circumferential sponge-portions and which are arranged at pre-determined inwardly spaced locations relative to further opposite (end extending) edges 87 and 89 of the patch 82.

Figure 7C:
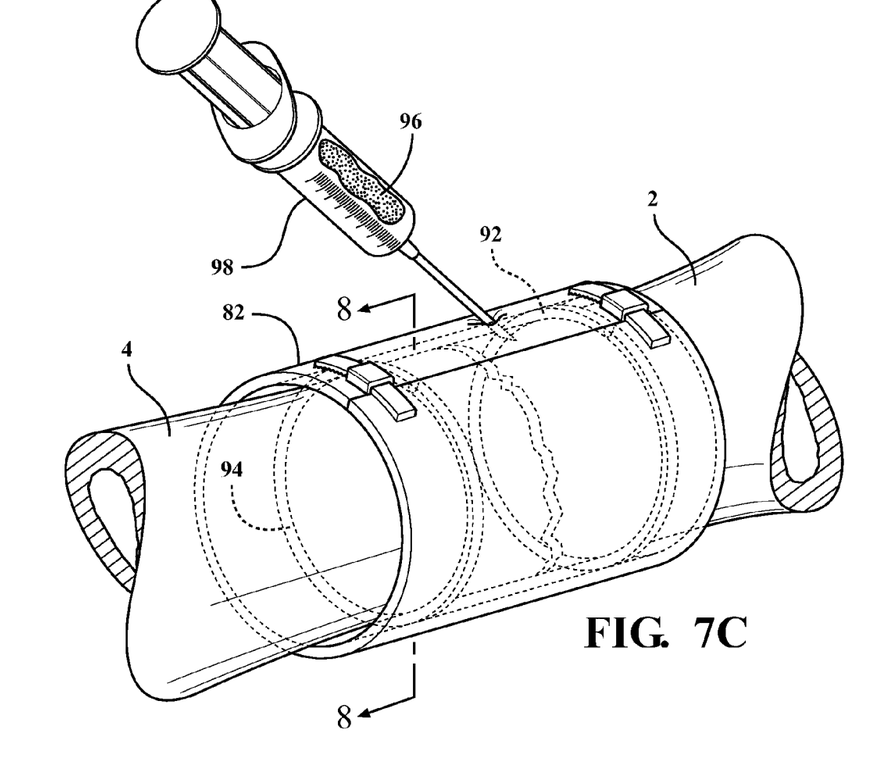
FIG. 7C is a succeeding illustration, similar to that shown in FIG. 7A, and illustrating a settable viscous composition which is administered through a needle injection through the exterior sleeve and into a coaxial and sleeve-shaped interior volume defined between the sleeve and the exposed bone surface, and further limited by the internally projecting boundary portions.
Figure 8:
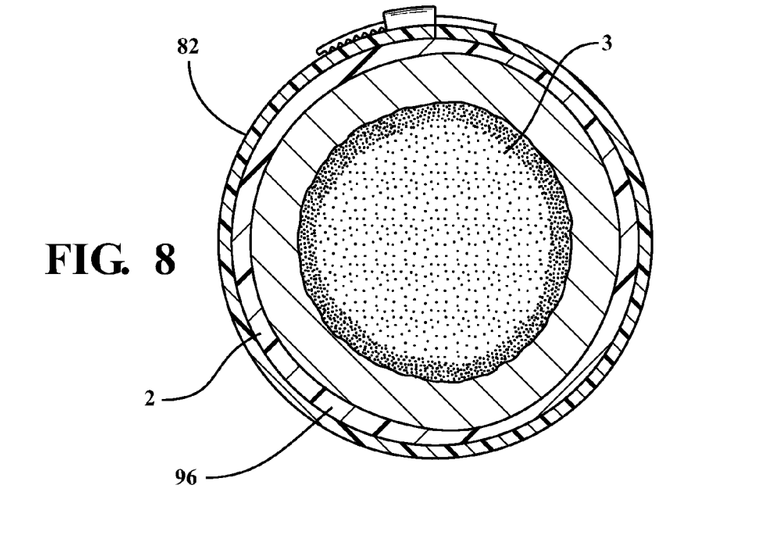
FIG. 8 is a cross sectional cutaway view taken along line 8-8 of FIG. 7C and illustrating in two dimension the exteriorly applied and bonding nature of the injected glue along an intermediate location of the patch proximate the bone fracture zone.

As further shown in FIG. 7C, which is a succeeding illustration to that shown in FIG. 7A, further illustrated is a settable viscous composition 96 which is administered through a syringe/needle 98 injection, such as which pierces through the exterior applied sleeve 82 and into a coaxial and sleeve-shaped interior volume defined between the sleeve 82 and the exposed bone surface, as further limited by the internally projecting boundary portions 92 and 94 which compress about the bone surface and define an enclosed inner pocket for receiving the composition 96. FIG. 8 is a cross sectional cutaway view taken along line 8-8 of FIG. 7C and illustrating in two dimension the exteriorly applied and bonding nature of the injected glue 96 inserted within and along the intermediate location of the patch 82 proximate the bone fracture zone and further limited in its linear expansion by the spaced apart and circumferentially encircling boundary portions 92 and 94. Also depicted in FIG. 8 is the configuration of selected bone section 2 with inner marrow 3 applicable to each of the operative embodiments described herein.

The construction of the plastic (including composite) material of the patch 82 is sufficiently ductile for application around the exterior bone fracture, yet sufficiently durable to support a user's weight during normal activity corresponding to the healing period. Upon drying and curing of the glue 96, the patch 82 can exhibit a bond-resistant inner surface which permits the patch to be removed to reveal a permanent bonding/covering material. Alternatively, the patch 82 can be formed of a material which bonds with the glue and can be left in place.

Figure 9:
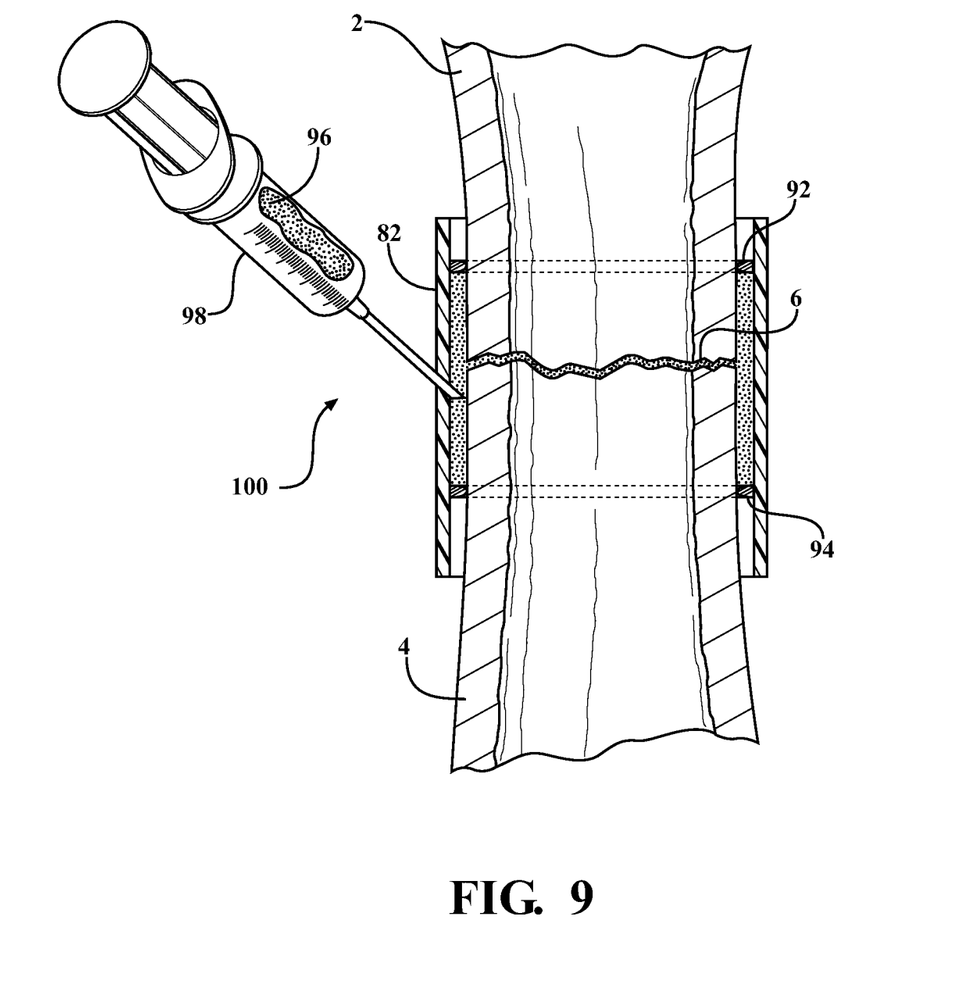
FIG. 9 is a plan view illustration in partially transparent fashion and illustrating the exteriorly supported patch design of FIG. 7 in use in combination with an internal scissor mechanism.

Referring finally to FIG. 9, a plan view illustration is generally shown at 100 in partially transparent fashion and illustrating the exteriorly supported patch design of FIG. 7 in use in combination with an internal scissor mechanism such as drawn from one of the previously described embodiments.

Having described my invention, other additional and preferred embodiments will become apparent to those skilled in the art to which it pertains, and without deviating from the scope of the appended claims.

I claim:

1. A cast system for aligning and supporting first and second interior bone locations adjoining a bone fracture zone, comprising:
    a body adapted to being employed against the interior bone locations surrounding the fracture zone;
    said body having an internally inserted membrane, said membrane including an interiorly supported and outwardly expandable scissor mechanism;
    said body providing for at least one of aligning the bone locations on either side of the fracture zone and influencing the bone locations in a compressive fashion against the fracture zone during healing of the bone; and
    an additional body further including a patch constructed of a sufficiently flexible and semi-rigid material adapted to be applied over exterior bone locations adjoining the bone fracture zone.

2. The cast system as described in claim 1, wherein said membrane comprises an inflatable bladder.

3. The cast system as described in claim 2, wherein said membrane comprises a plurality of elongate stiffening members.

4. The cast system as described in claim 1, wherein said patch further comprises linear end-projecting and serrated engaging straps extending from a first exposed edge and engaging through opposing end situated receiving hooks.

5. The cast system as described in claim 4, further comprising interior positioned, spaced apart and circumferentially surface extending boundary portions applied along an inner and bone contacting surface of said patch.

6. The cast system as described in claim 5, further comprising a settable viscous composition administered through a syringe/needle piercing through said patch and into a coaxial and sleeve-shaped interior volume defined between said patch and exposed bone surface, between said boundary portions.

7. A cast system for aligning and supporting first and second interior bone locations adjoining a bone fracture zone, comprising:
    a body adapted to being employed against the interior bone locations surrounding the fracture zone, said body further including an insertable membrane which integrates at least one elongated extending and stiffening member;
    said membrane further having an interiorly supported and outwardly expandable scissor mechanism;
    said body providing for at least one of aligning the bone locations on either side of the fracture zone and influencing the bone locations in a compressive fashion against the fracture zone during healing of the bone; and
    wherein said body further comprises a plurality of clips adapted to be secured to exterior bone locations adjoining the fracture zone and being actuated to influence the bone locations against the fracture zone.

8. The cast system as described in claim 7, wherein said membrane further comprises an inflatable bladder.

9. A cast system for aligning and supporting first and second bone locations adjoining a bone fracture zone, comprising:
    a patch constructed of a sufficiently flexible and semi-rigid material which is adapted to being applied over an exterior of the bone surrounding the fracture zone;
    said patch further comprising linear end-projecting and serrated engaging straps extending from a first exposed edge and engaging through opposing end situated receiving hooks;
    interior positioned, spaced apart and circumferentially surface extending boundary portions applied along an inner and bone contacting surface of said patch, a settable viscous composition administered through a syringe/needle piercing through said patch and into a coaxial and sleeve-shaped interior volume defined between said patch and exposed bone surface, between said internally projecting boundary portions; and
    said patch aligning the bone locations on either side of the fracture zone during healing of the bone.

10. A cast system for aligning and supporting first and second interior bone locations adjoining a bone fracture zone, comprising:
    a body adapted to being employed against the interior bone locations surrounding the fracture zone;

said body having an internally inserted membrane, said membrane including an interiorly supported and outwardly expandable scissor mechanism;

said body providing for at least one of aligning the bone locations on either side of the fracture zone and influencing the bone locations in a compressive fashion against the fracture zone during healing of the bone; and additional bodies each further including a plurality of clips adapted to be secured to exterior bone locations adjoining the fracture zone and being actuated to influence the bone locations against the fracture zone.

* * * * *

UNITED STATES PATENT AND TRADEMARK OFFICE
CERTIFICATE OF CORRECTION

| | | |
|---|---|---|
| PATENT NO. | : 8,562,550 B2 | Page 1 of 1 |
| APPLICATION NO. | : 12/785955 | |
| DATED | : October 22, 2013 | |
| INVENTOR(S) | : Miguel A. Linares | |

It is certified that error appears in the above-identified patent and that said Letters Patent is hereby corrected as shown below:

Title Page

Item (63) Related U.S. Application Data, Delete "May 24, 2010", Insert --May 26, 2010--

Signed and Sealed this
Twentieth Day of January, 2015

Michelle K. Lee
*Deputy Director of the United States Patent and Trademark Office*